(12) United States Patent
Chaves et al.

(10) Patent No.: US 6,223,748 B1
(45) Date of Patent: May 1, 2001

(54) PROTECTIVE EYE COVERING FOR INFANTS

(76) Inventors: Kay E. Chaves, 5403 W. Orlando Cir., Broken Arrow, OK (US) 74011; J. Jill Ruskoski, 9524 S. Lakewood Ave., Tulsa, OK (US) 74137

( * ) Notice: Subject to any disclaimer, the term of this patent is extended or adjusted under 35 U.S.C. 154(b) by 0 days.

(21) Appl. No.: 09/636,607

(22) Filed: Aug. 11, 2000

(51) Int. Cl.$^7$ .................................................. A61F 11/00
(52) U.S. Cl. ............................. 128/857; 128/858; 2/10; 2/15
(58) Field of Search ................................ 128/846, 857, 128/858; 2/10, 15

(56) References Cited

U.S. PATENT DOCUMENTS

| D. 258,532 | 3/1981 | Wagner . | |
| D. 285,624 | 9/1986 | Rosenbaum . | |
| 3,780,379 | 12/1973 | Kampman . | |
| 4,411,263 | * 10/1983 | Cook | 128/858 |
| 4,502,476 | * 3/1985 | Welt | 128/858 |
| 4,644,588 | * 2/1987 | Zawacki | 128/858 |
| 4,790,031 | * 12/1988 | Duerer | 2/15 |
| 5,183,059 | * 2/1993 | Leonardi | 128/858 |
| 5,613,502 | * 3/1997 | Lee | 128/858 |

* cited by examiner

Primary Examiner—Michael A. Brown

(57) ABSTRACT

A protective eye covering for infants for safely securing a protective eye covering for infants during photo-therapy. The protective eye covering for infants includes a mask having padding material sandwiched between outer layers of material and being adapted to removably cover over an infant's eyes during photo-therapy; and also includes a strap assembly for fastening the mask about an infant's head.

8 Claims, 2 Drawing Sheets

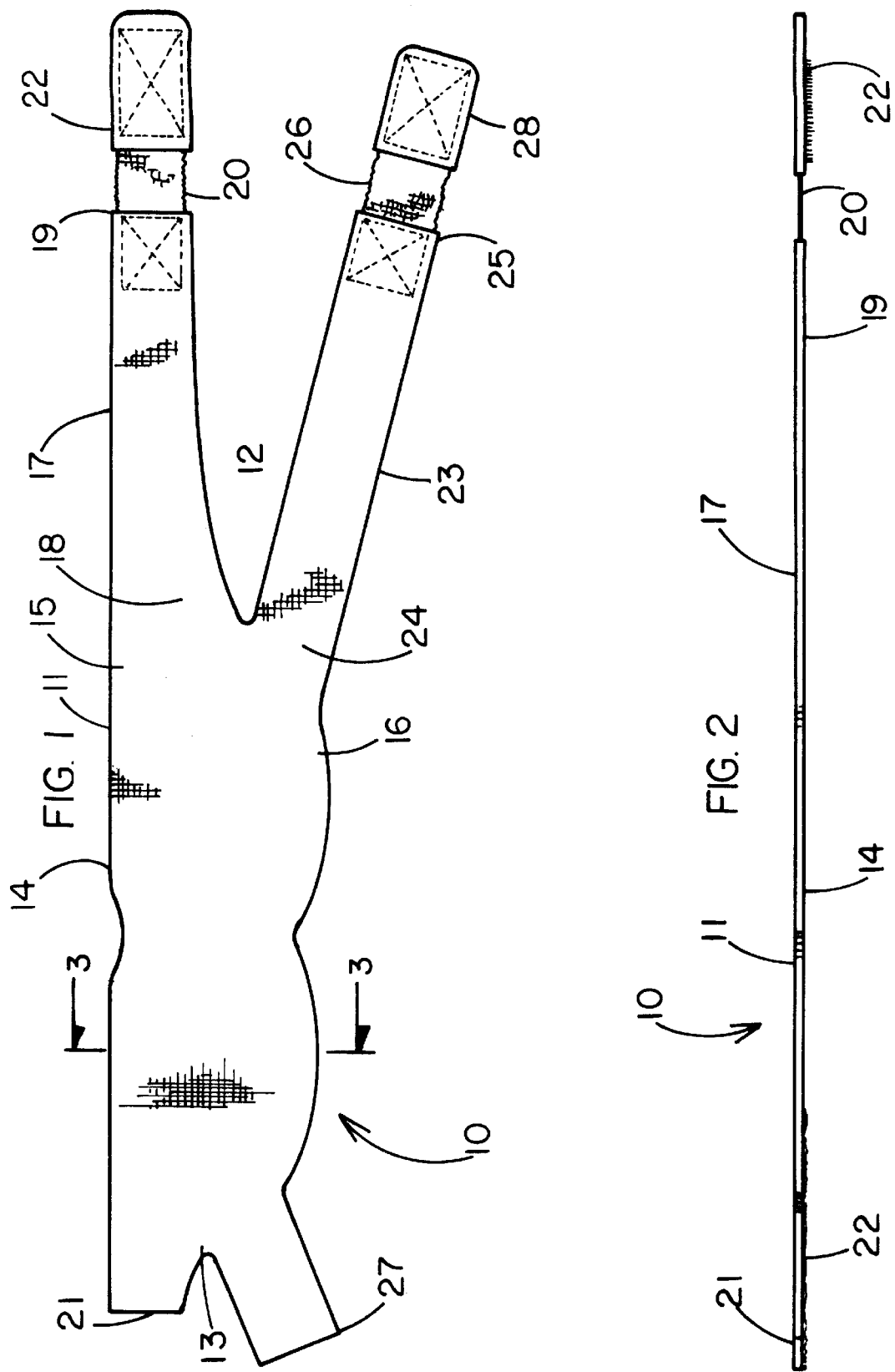

PROTECTIVE EYE COVERING FOR INFANTS

BACKGROUND OF THE INVENTION

1. Field of the Invention

The present invention relates to non-slip eye shades for infants and more particularly pertains to a new protective eye covering for infants for safely securing a protective eye covering for infants during photo-therapy.

2. Description of the Prior Art

The use of non-slip eye shades for infants is known in the prior art. More specifically, non-slip eye shades for infants heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,411,263; U.S. Pat. No. 5,613,502; U.S. Pat. No. 4,644,588; U.S. Pat. No. Des. 285,624; U.S. Pat. No. Des. 258,532; and U.S. Pat. No. 3,780,379.

While these devices fulfill their respective, particular objectives and requirements, the aforementioned patents do not disclose a new protective eye covering for infants. The inventive device includes a mask having padding material sandwiched between outer layers of material and being adapted to removably cover over an infant's eyes during photo-therapy; and also includes a strap assembly for fastening the mask about an infant's head.

In these respects, the protective eye covering for infants according to the present invention substantially departs from the conventional concepts and designs of the prior art, and in so doing provides an apparatus primarily developed for the purpose of safely securing a protective eye covering for infants during photo-therapy.

SUMMARY OF THE INVENTION

In view of the foregoing disadvantages inherent in the known types of non-slip eye shades for infants now present in the prior art, the present invention provides a new protective eye covering for infants construction wherein the same can be utilized for safely securing a protective eye covering for infants during photo-therapy.

The general purpose of the present invention, which will be described subsequently in greater detail, is to provide a new protective eye covering for infants which has many of the advantages of the non-slip eye shades for infants mentioned heretofore and many novel features that result in a new protective eye covering for infants which is not anticipated, rendered obvious, suggested, or even implied by any of the prior art non-slip eye shades for infants, either alone or in any combination thereof.

To attain this, the present invention generally comprises a mask having padding material sandwiched between outer layers of material and being adapted to removably cover over an infant's eyes during photo-therapy; and also includes a strap assembly for fastening the mask about an infant's head.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new protective eye covering for infants which has many of the advantages of the non-slip eye shades for infants mentioned heretofore and many novel features that result in a new protective eye covering for infants which is not anticipated, rendered obvious, suggested, or even implied by any of the prior art non-slip eye shades for infants, either alone or in any combination thereof.

It is another object of the present invention to provide a new protective eye covering for infants which may be easily and efficiently manufactured and marketed.

It is a further object of the present invention to provide a new protective eye covering for infants which is of a durable and reliable construction.

An even further object of the present invention is to provide a new protective eye covering for infants which is susceptible of a low cost of manufacture with regard to both materials and labor, and which accordingly is then susceptible of low prices of sale to the consuming public, thereby making such protective eye covering for infants economically available to the buying public.

Still yet another object of the present invention is to provide a new protective eye covering for infants which provides in the apparatuses and methods of the prior art some of the advantages thereof, while simultaneously overcoming some of the disadvantages normally associated therewith.

Still another object of the present invention is to provide a new protective eye covering for infants for safely securing a protective eye covering for infants during photo-therapy.

Yet another object of the present invention is to provide a new protective eye covering for infants which includes a mask having padding material sandwiched between outer layers of material and being adapted to removably cover over an infant's eyes during photo-therapy; and also includes a strap assembly for fastening the mask about an infant's head.

Still yet another object of the present invention is to provide a new protective eye covering for infants that is easy and quick to use without any harm to the infants.

Even still another object of the present invention is to provide a new protective eye covering for infants that is easy to attach and detach from about the heads of the infants.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of a new protective eye covering for infants according to the present invention.

FIG. 2 is an edge elevational view of the present invention.

DESCRIPTION OF THE PREFERRED EMBODIMENT

Figure 3:
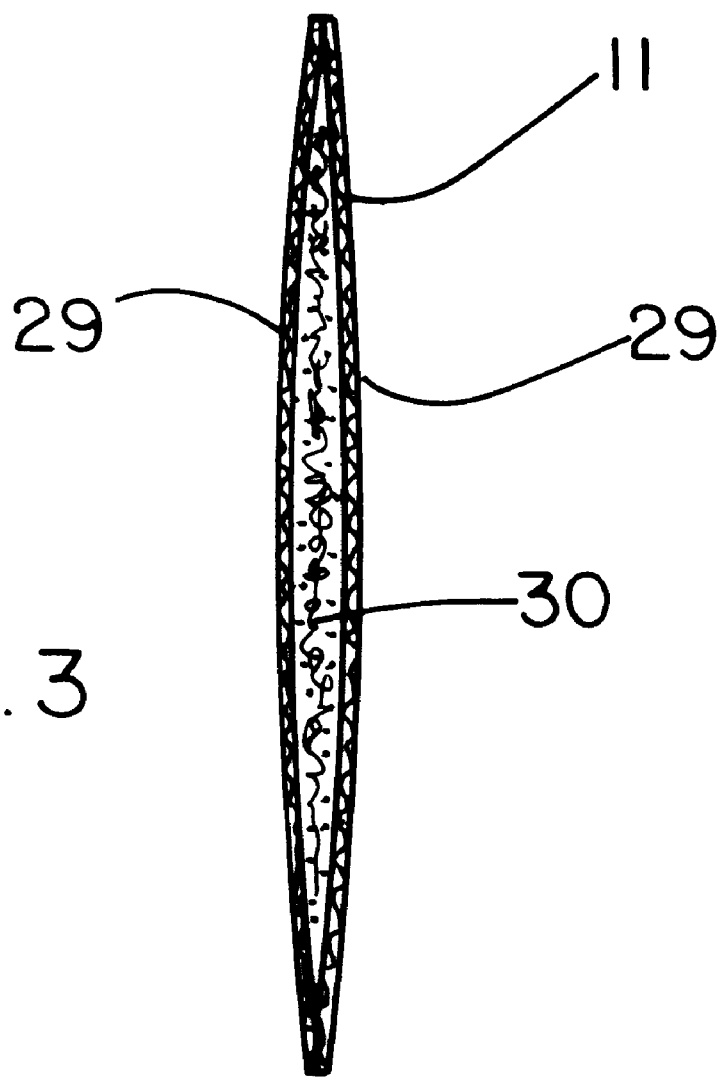
FIG. 3 is a cross-sectional view of the mask of the present invention.

With reference now to the drawings, and in particular to FIGS. 1 through 3 thereof, a new protective eye covering for infants embodying the principles and concepts of the present invention and generally designated by the reference numeral 10 will be described.

As best illustrated in FIGS. 1 through 3, the protective eye covering for infants 10 generally comprises a mask 11 having padding material 30 sandwiched between outer layers of material 29 and being adapted to removably cover over an infant's eyes during photo-therapy. A strap assembly for fastening the mask 11 about an infant's head includes first and second strap members 17,23 having first ends 18,24 integrally attached to a first side edge 12 of the mask 11, and also includes first and second strap support members 21,27 being integrally attached to a second side edge 13 of the mask 11, and further includes first and second elastic members 20,26 being securely and conventionally attached and sewn to second ends 19,25 of the first and second strap members 17,23, and also includes first and second fastening members 22,28 securely and conventionally attached and sewn to the first and second elastic members 20,26 and to the first and second strap support members 21,27 for fastening the first and second strap members 17,23 about the infant's head. The first strap member 17 is securely attached to an upper portion 15 of the mask 11 and extends generally parallel to a top edge 14 of the mask 11 with the first strap member 17 having a top edge which is aligned generally continuous with the top edge 14 of the mask 11. The first strap member 17 is adapted to extend in a plane of the mask 11 about the infant's head with the first strap member 17 being fastenable about the user's head directly at a same level as and directly behind the mask 11 and above an occipital bone of the user's head. The first strap support member 21 has a top edge which is aligned generally continuous with the top edge 14 of the mask 11 and is adapted to fasten to the first elastic member 20. The second strap member 23 is generally attached to a lower portion 16 of the mask 11 and extends outwardly and downwardly at an angle relative to the first strap member 17 and is adapted to fasten below the occipital bone of the infant's head to essentially prevent the protective eye covering 10 from slipping off from the user's head. The second strap support member 27 is generally attached to the lower portion 16 of the mask 11 and extends outwardly and downwardly relative to the first strap support member 17 and is adapted to fasten to the second elastic member 26 with the first and second fastening members 22,28 being essentially strips of hook and loop fasteners.

In use, the user places the mask 11 over the eyes of the infant and extends the first strap member 17 directly behind the infant's head and attaches the first elastic member 20 to the first strap support member 21 using the first fastening members 22, and then extends the second strap member 23 below the occipital bone of the back of the infant's head and attaches the second elastic member 26 to the second strap support member 27 to secure the protective eye covering 10 to the infant's head with slippage.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A protective eye covering for infants comprising:
    a mask having padding material sandwiched between outer layers of material and being adapted to removably cover over an infant's eyes during photo-therapy; and
    a strap assembly for fastening said mask about an infant's head, said strap assembly including first and second strap members having first ends integrally attached to a first side edge of said mask, and also includes first and second strap support members being integrally attached to a second side edge of said mask, and further includes first and second elastic members being securely attached to second ends of said first and second strap members, and also includes first and second fastening members securely attached to said first and second elastic members and to said first and second strap support members for fastening said first and second strap members about the infant's head.

2. A protective eye covering for infants as described in claim 1, wherein said first strap member is securely attached to an upper portion of said mask and extends generally parallel to a top edge of said mask.

3. A protective eye covering for infants as described in claim 2, wherein said first strap member has a top edge which is aligned generally continuous with said top edge of said mask, said first strap member being adapted to extend in a plane with said mask about the infant's head, said first strap member being fastenable about the user's head directly at a same level as and behind said mask.

4. A protective eye covering for infants as described in claim 3, wherein said first strap support member has a top edge which is aligned generally continuous with said top edge of said mask and is adapted to fasten to said first elastic member.

5. A protective eye covering for infants as described in claim 1, wherein said second strap member is generally attached to a lower portion of said mask and extends outwardly and downwardly at an angle relative to said first strap member and is adapted to fasten below an occipital bone of the infant's head to essentially prevent said protective eye covering from slipping off or down from the user's head.

6. A protective eye covering for infants as described in claim 5, wherein said second strap support member is generally attached to said lower portion of said mask and extends outwardly and downwardly relative to said first strap support member and is adapted to fasten to said second elastic member.

7. A protective eye covering for infants as described in claim 6, wherein said first and second fastening members are essentially strips of hook and loop fasteners.

8. A protective eye covering for infants comprising:
a mask having padding material sandwiched between outer layers of material and being adapted to removably cover over an infant's eyes during photo-therapy; and
a strap assembly for fastening said mask about an infant's head including first and second strap members having first ends integrally attached to a first side edge of said mask, and also including first and second strap support members being integrally attached to a second side edge of said mask, and further including first and second elastic members being securely attached to second ends of said first and second strap members, and also including first and second fastening members securely attached to said first and second elastic members and to said first and second strap support members for fastening said first and second strap members about the infant's head, said first strap member being securely attached to an upper portion of said mask and extends generally parallel to a top edge of said mask, said first strap member having a top edge which is aligned generally continuous with said top edge of said mask, said first strap member being adapted to extend in a plane with said mask about the infant's head, said first strap member being fastenable about the user's head directly at a same level as and behind said mask and above an occipital bone of the infant's head, said first strap support member having a top edge which is aligned generally continuous with said top edge of said mask and is adapted to fasten to said first elastic member, said second strap member being generally attached to a lower portion of said mask and extending outwardly and downwardly at an angle relative to said first strap member and being adapted to fasten below the occipital bone of the infant's head to essentially prevent said protective eye covering from slipping off or down from the user's head, said second strap support member being generally attached to said lower portion of said mask and extending outwardly and downwardly relative to said first strap support member and being adapted to fasten to said second elastic member, said first and second fastening members being essentially strips of hook and loop fasteners.

* * * * *